United States Patent [19]

Grim

[11] Patent Number: 5,092,319
[45] Date of Patent: Mar. 3, 1992

[54] ANKLE BRACE WITH ADJUSTABLE SHOELACE ATTACHMENT

[75] Inventor: Tracy E. Grim, Broken Arrow, Okla.

[73] Assignee: Royce Medical Company, Culver City, Calif.

[21] Appl. No.: 649,704

[22] Filed: Feb. 1, 1991

[51] Int. Cl.$^5$ .................... A61F 3/00; A61F 13/06; A61F 5/37
[52] U.S. Cl. .................... 602/27; 128/882
[58] Field of Search .................... 128/882, 80 H, 166, 128/80 C, 80 E, 80 F, 80 G, 80 A, 80 D, 402

[56] References Cited

U.S. PATENT DOCUMENTS

| | | | |
|---|---|---|---|
| 4,817,589 | 4/1989 | Wertz | 128/80 H |
| 4,844,094 | 7/1989 | Grim | 128/80 H |
| 4,869,267 | 9/1989 | Grim | 128/80 H |
| 4,964,402 | 10/1990 | Grim | 128/402 |
| 4,966,134 | 10/1990 | Brewer | 128/882 |

*Primary Examiner*—Robert A. Hafer
*Assistant Examiner*—Michael Brown
*Attorney, Agent, or Firm*—Poms, Smith, Lande & Rose

[57] ABSTRACT

An ankle brace is shown which is inserted into a laced shoe. The brace includes side supports with padding between the supports and ankle for immobilizing the inversion and eversion movement of the ankle. Ties or straps are used to secure the supports on either side of the ankle while the lower portion of each support is secured within the shoe by attachments to which the shoelaces may be engaged. The inventive improvement rests in the design of the attachments which are mounted in a plurality of apertures which may include a series of circular apertures or a slot having semicircular apertures along one or both edge. Each attachment includes a middle portion from which a protuberance extends for engagement with one of the apertures. The attachment may then be secured in one of the apertures by a fastener. The fastener may be formed by either deforming a lower portion of the attachment or by use of a threaded fastener, such as a screw.

23 Claims, 4 Drawing Sheets

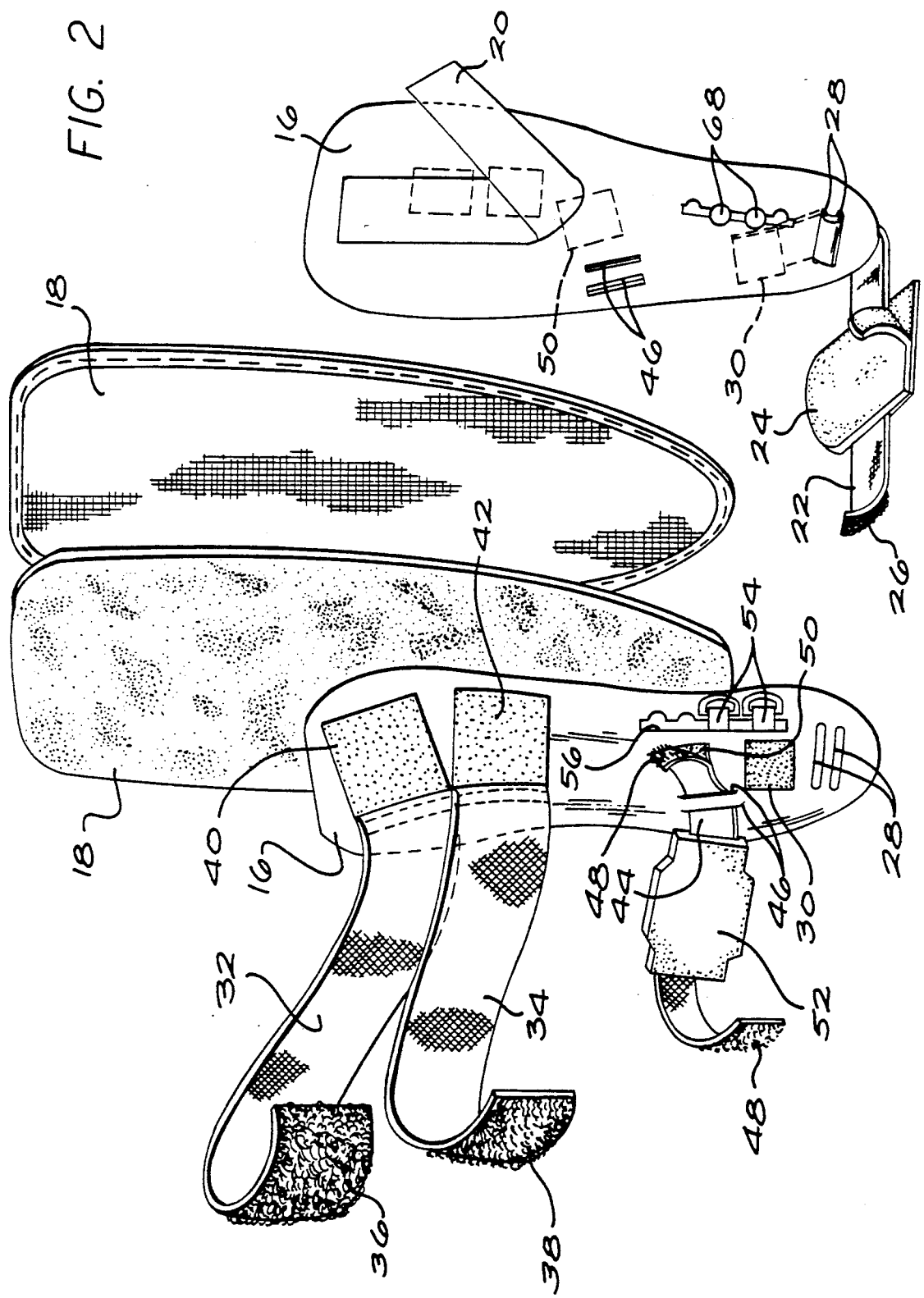

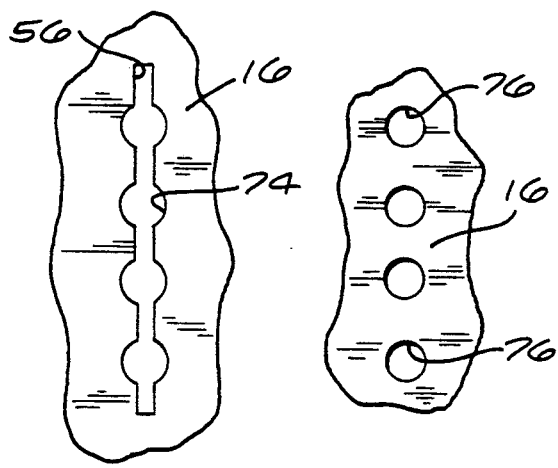
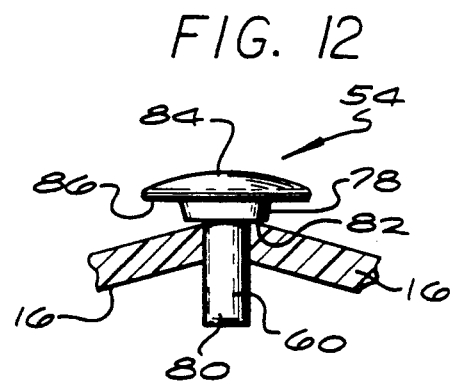
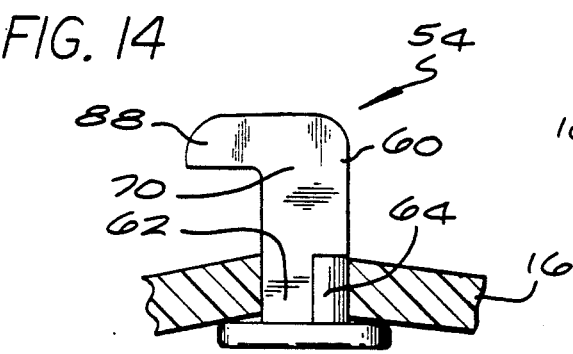
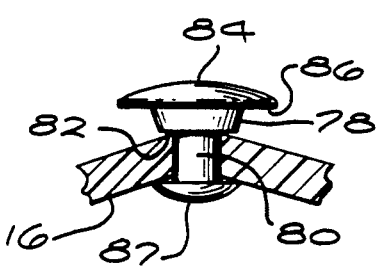
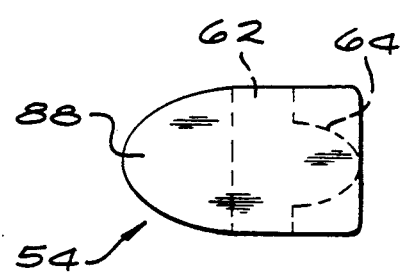
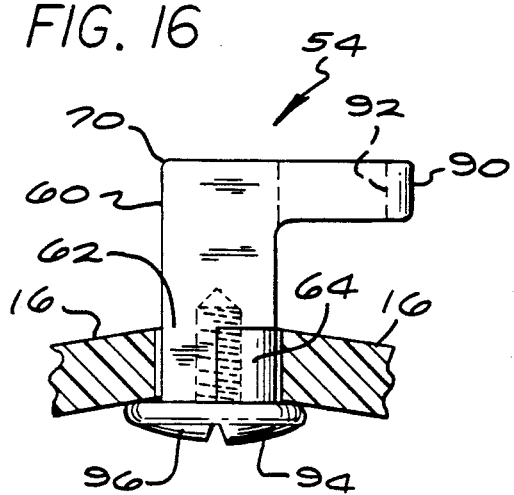
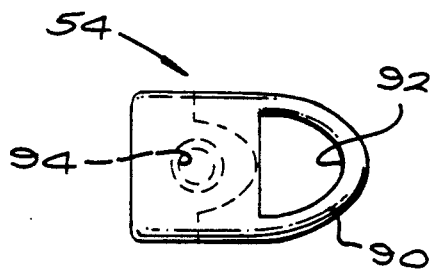

ANKLE BRACE WITH ADJUSTABLE SHOELACE ATTACHMENT

BACKGROUND OF THE INVENTION

1. Field of the Invention

The present invention relates to an orthopedic device and, more particularly, to an ankle brace for stabilizing the ankle after an injury. More specifically, the present invention relates to an ankle brace of the type having rigid side supports which fit into the top of a laced shoe, wherein the ankle brace is retained within the shoe by attaching the shoelaces to adjustable attachments on the side supports.

2. Description of Prior Art

It is well known in the art to utilize an ankle brace upon the ankle of an individual who has injured that ankle by spraining the tendons or ligaments therein. It is generally desirable to immobilize the ankle against inversion or eversion while permitting plantar-flexion and dorsi-flexion. An ankle brace which accomplishes the immobilization of inversion and eversion while permitting plantar-flexion and dorsi-flexion is shown in U.S. Pat. No. 4,844,094, which issued Jul. 4, 1989, by T. E. Grim, which is assigned to the assignee of the present invention.

Ankle braces have been further improved by substituting a gel pad for the padding normally found between the rigid side supports and the user's ankle. This gel pad may be used to either generate heat or cold about the wearer's ankle, depending upon the type of therapy desired. A patent showing such a device is shown in U.S. Pat. No. 4,964,402, issued Oct. 23, 1990, by T. E. Grimm, also assigned to the assignee of the present invention.

Each of these patents utilizes an attachment or fastening device at the distal end of the rigid side supports for receiving shoelaces which, in turn, help to retain the ankle brace within the shoe. The wearer of the ankle brace may have a foot size or a shoe style that causes the lace eyelets to be aligned at a different height along the front of the shoe. When the position of the attachments is fixed as in the prior art patents discussed above or in other prior art ankle braces, it is sometimes difficult to align the shoelaces with the attachments.

SUMMARY OF THE INVENTION

Accordingly, it is an object of the present invention to provide an ankle brace with an adjustable shoelace attachment.

It is another object of the present invention to provide an adjustable attachment which may be adjusted into a plurality of different positions and, once the desired position has been established, securely fastened to the rigid side support of the ankle brace.

In accomplishing these and other objects, there is provided a plurality of apertures within the lower portion of each of the rigid side supports of the ankle brace. Attachments having extended protuberances are engaged within selected ones of the apertures so that the extended protuberances engage with and are retained therein. A fastener is then used to fasten each attachment within the selected aperture for securing the attachment in its desired position.

BRIEF DESCRIPTION OF THE DRAWINGS

A better understanding of the present invention and of the objects and advantages thereof will be had after careful consideration of the following specification and drawings, wherein:

FIG. 2 is an exploded view showing the components of the ankle brace;

FIG. 10 is a partial side view of a rigid side support showing a second embodiment of a plurality of apertures in a slot that receives an attachment;

FIG. 11 is a partial side view, similar to FIG. 10, showing another embodiment of a plurality of apertures that received an attachment;

FIG. 12 is a side view of a second embodiment of the attachment;

FIG. 13 is a side view of the attachment shown in FIG. 12 after its lower portion has been deformed;

FIG. 14 is a side view of a third embodiment of the attachment;

FIG. 15 is a top view of the attachment shown in FIG. 14;

FIG. 16 is a side view of a fourth embodiment of the attachment; and

FIG. 17 is a top view of the attachment shown in FIG. 16.

DESCRIPTION OF THE PREFERRED EMBODIMENTS

Figure 1:
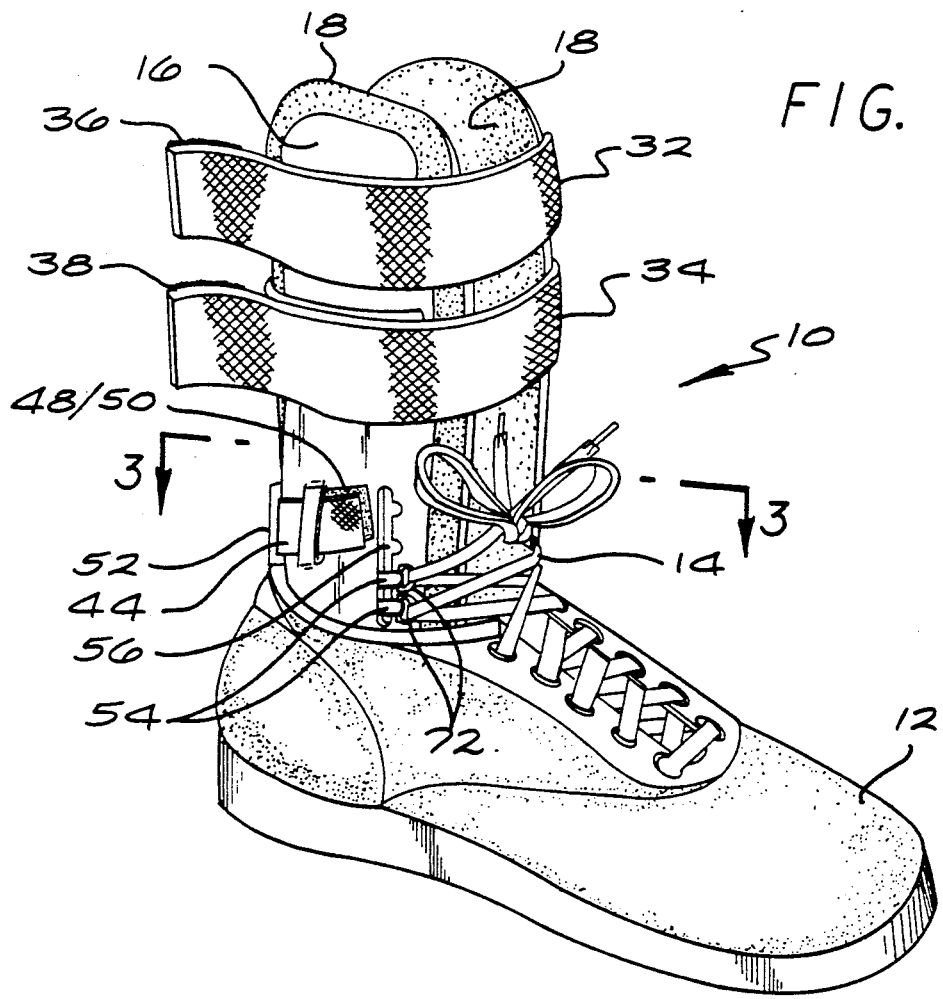
FIG. 1 is a perspective view of the ankle brace incorporation the present invention fitted within a laced shoe.

As shown in FIG. 1, an ankle brace 10 of the present invention is fitted within a shoe 12 having shoelaces 14. The ankle brace includes a pair of rigid side support members 16 made of a plastic material that may be vacuum formed to conform to the shape of the lower leg and ankle. Positioned between the rigid supports 16 and the ankle are a pair of resilient pads 18. Pads 18 may be made from a dense foam material or from a gel material which may be used for cold temperature therapy or for hot temperature therapy as described in U.S. Pat. No. 4,964,402. The resilient pads 18 may be attached to the inside of the side supports 16 as by double-sided adhesive tape 20 or some other material such as that sold under the trademark Velcro, FIG. 2.

Interconnecting the two side supports 16 is a bottom strap or tie 22 which includes a pad 24 and an attachment pad 26 on each end such as a pad of attachment material sold under the trademark Velcro. The bottom strap 22 passes through a pair of slots 28 in the lower portions of rigid side supports 16 where the attachment pads 26 may be attached to each side support 16 by second attachment pads 30.

In addition to the bottom strap, a pair of upper strap members 32 and 34 having attachment pads 36 and 38, respectively, are attached to the upper portion of one of the side supports 16. These straps may be wrapped about the leg below the calf and attached to their opposite ends by attaching the attachment pads 36 and 38 to appropriate pad receptors 40 and 42. The upper straps serve to secure the ankle brace. However, it was found in U.S. Pat. No. 4,844,094 that additional tie straps were required about the lower portion of the rigid side supports 16. This lower tie strap 44 is attached in a manner similar to bottom strap 22, in that it passes through a pair of slots 46 where an attachment pad 48 is secured to a pad receptor 50. It will be seen in FIG. 2 that the lower strap 44 has attachment pads 48 at each end, while a heel cushion pad 52 prevents the lower strap 44 from cutting into the wearer's heel.

Figure 4:
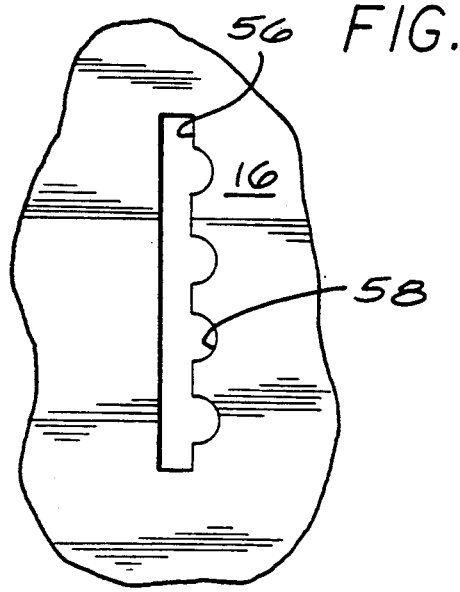
FIG. 4 is a partial side view of a rigid side support showing a plurality of apertures joined by a slot that receives an attachment.

The ankle brace is completed by a set of shoelace attachments 54 which are adjustably received within a plurality of apertures formed in a slot 56 best seen in FIG. 4. In the preferred embodiment, only a single attachment 54 is placed in each slot 56 although two such attachments 54 are shown in each slot to illustrate that more than one attachment may be used therein. Also, in one embodiment, the slot 56 includes a plurality of semicircular apertures or notches 58 which form serrations along one edge of slot 56. It will be understood by those skilled in the art that other shapes may be used to form the apertures or notches 58 and that the notches may be arranged on one or both sides of slot 56. See, for example, FIGS. 10 and 11. As a further example, a diamond-like notch could be cut with triangles formed on either side of slot 56.

Figure 3:
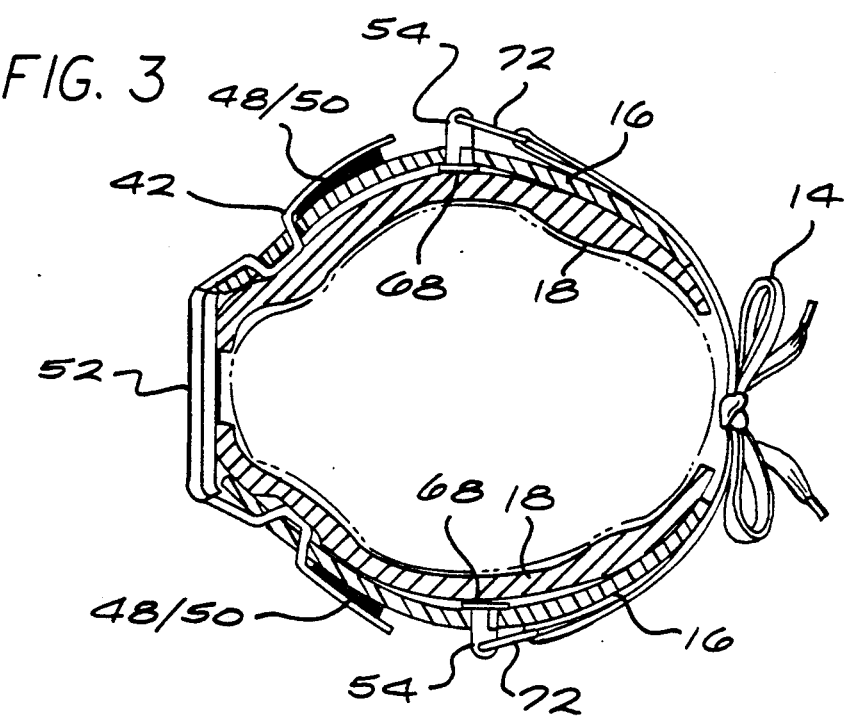
FIG. 3 is a cross-sectional view taken along line 3—3 of FIG. 1.
Figure 5:
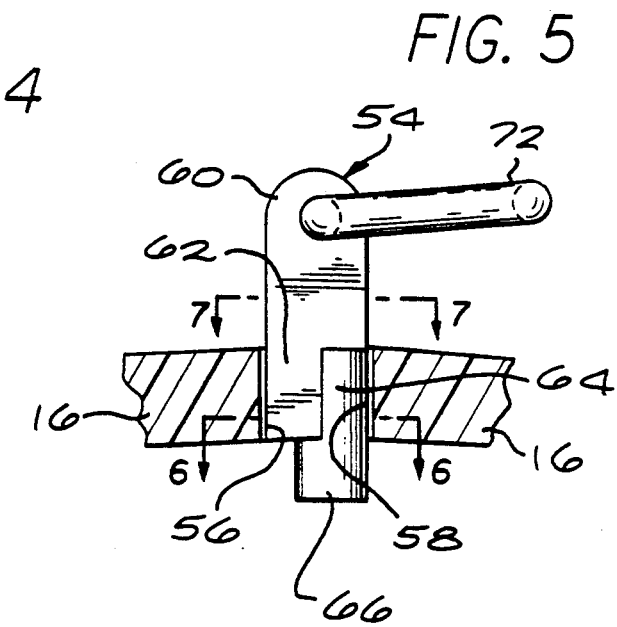
FIG. 5 is a partial side view of an attachement.
Figure 6:
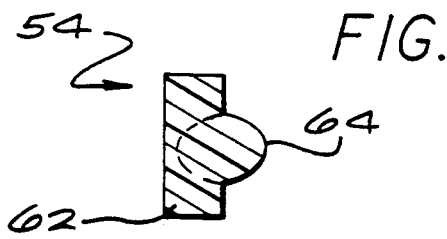
FIG. 6 is a cross-sectional view taken along line 6—6 of FIG. 5.
Figure 7:
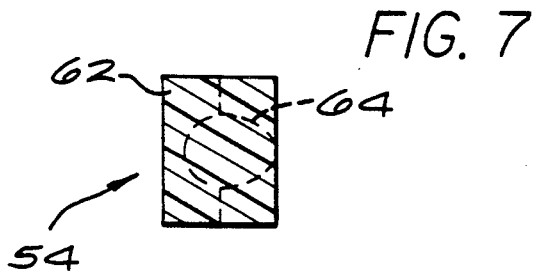
FIG. 7 is a second cross-sectional view taken along line 7—7 of FIG. 5.
Figure 8:
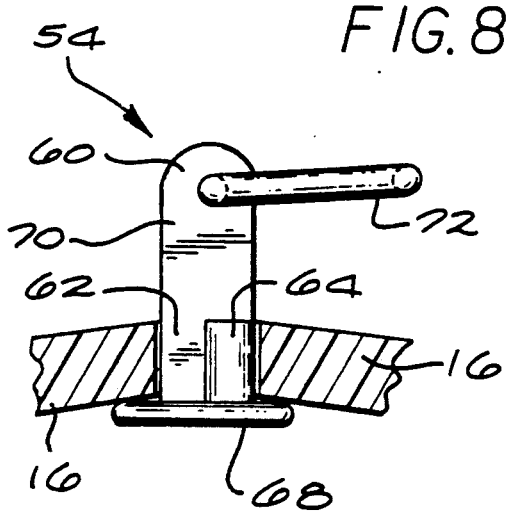
FIG. 8 is a side view of the attachment shown in FIG. 5 after its lower portion has been deformed.
Figure 9:
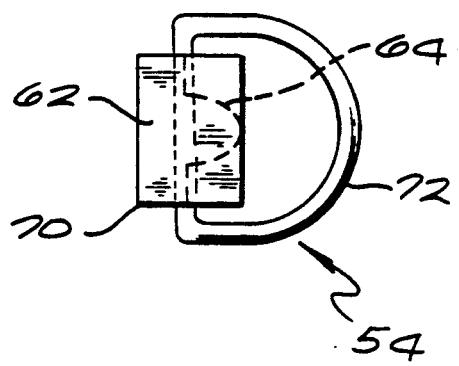
FIG. 9 is a top view of the attachment shown in FIG. 8.

Similarly, many variations of the attachment 54 may be utilized including those shown in FIGS. 5-9 and 12-17. The attachment shown in FIGS. 1-3 is shown in greater detail in FIG. 5, including a molded column 60 formed with an upper, middle, and lower portion. The middle portion, best seen in FIG. 6, includes a rectangular cross-sectional portion 62 having four sides with a semicircular protuberance 64 extending from one surface of the rectangular cross-sectional portion 62. It will be seen from FIG. 5 that the rectangular cross-sectional portion 62 rides within slot 56 while the semicircular protuberance 64 extends into the semicircular notch 58 of slot 56. Extending from the lower surface of the middle portion of column 60 and coaxially with the semicircular protuberance 64 is a lower portion or post 66. The post 66 may be made of a suitable material that may be deformed when heated, for example, so that the application of heat to post 66 will cause the cylindrical structure to deform and swage over to form a rivet-like head 68, as seen in FIGS. 8, 13 and 14. As seen in FIGS. 5, 8 and 9, the upper portion 70 of the column 60 may be provided with an aperture to receive a D-ring 72. The D-ring may pass completely through the upper portion 70 of column 60 for securing the shoelaces 14, as best seen in FIG. 1.

Another embodiment of the slot 56 is shown in FIG. 10 wherein the slot 56 has a plurality of semicircular apertures 74 on each edge thereof. Further, the slot may be eliminated by simply using a plurality of circular apertures 76 aligned vertically along a vertical axis generally parallel to the longitudinal axis of the rigid side support 16, as shown in FIG. 11.

An attachment 54 formed as an axisymmetrical column 60 is shown in FIG. 12 having a middle portion 78 that is circular in cross-section and a post 80 extending from the middle portion that is also circular in cross-section which forms a lower portion or protuberance with a shoulder 82 between middle and lower portions. Shoulder 82 rests upon the outer surface of side support 16 at a selected one of either the semicircular apertures 74 or circular apertures 76. The attachment 54 is completed by an upper portion formed as an extending head 84 which forms a second shoulder 86 between the head 84 and middle portion 78. A shoelace 14 is engaged under shoulder 86, against middle portion 78, and the outer surface side support 16 for retention by the attachment 54. As seen in FIG. 13, the lower portion or post 80 may be deformed, as by heat, and swaged over onto the lower surface of side support 16 for retaining the attachment 54 in the selected aperture by forming a rivet-like head 87.

In place of the D-ring 72 shown in FIGS. 5, 8, and 9 or the extended head 84 shown in FIGS. 12 and 13, the upper portion 70 of column 60 may be laterally extended, as shown in FIGS. 14 and 15, to form a shoe hook 88. The shoe hook portion 88 extends in one direction away from the upper portion 70 so that shoelace 14 is retained between the extension 88, the upper portion 70 of column 60, and the outer surface of side support 16.

As seen in FIGS. 16 and 17, another embodiment of the attachment column 60 includes an extension 90 of the upper portion 70 which has been relieved to form an aperture 92 therein. The aperture 92 forms an eyelet similar to the eyelet formed by the D-ring 72 for receiving a shoelace 14. In another embodiment, it will be seen in FIG. 16 that the lower portion or post 66 of column 60 may be removed and the lower surface of the rectangular cross-sectional, middle portion 62 and its semicircular protuberance 64 provided with a threaded aperture 94 which receives a threaded fastener such as a pan-head screw 96. The screw 96 may be provided with a deformable insert in its threaded portions to establish a locking feature once it has been inserted into the threaded aperture 94.

It may now be seen that the ankle brace 10 may be assembled within the shoe 12. Depending upon the design of the shoe 12, it may be desirable for the wearer to adjust the attachments 54 by moving the column 60 so that each rectangular cross-sectional middle portion 62 is fully secured within slot 56 and the semicircular protuberance 64 is selectively secured within one of the semicircular notches 68 found in slot 56 (FIG. 4). In another embodiment the attachment 54 is moved until its middle portion 78 is engaged against a selected aperture 74 or 76 and the post protrudes into the selected aperture (FIGS. 10 or 11). Once the appropriate location of each attachment 54 has been established, the attachment may be permanently affixed within the selected aperture 74 or 76 by swaging the protuberance or lower post 80 to form the rivet-like head 87. Alternately, in another embodiment, the screw 96 may be inserted into the threaded aperture 94 and locked therein by a suitable locking arrangement such as the deformable insert described above, bonding material, or a lock washer.

In addition to the variations in the configuration of the apertures 58, 74, and 76 described above and the variations of the attachments 54 shown in FIGS. 5-9 and 12-17, other modifications and variations of the present invention will become apparent to those skilled in the art. Accordingly, the present invention should be limited only by the appended claims.

I claim:

1. In an ankle brace for insertion into a shoe with shoelaces for immobilizing the ankle against inversion or eversion while permitting plantar-flexion and dorsi-flexion, including a pair of rigid side supports for supporting the ankle, pads mounted on the inside of said rigid side supports to cushion the ankle, attachment straps to secure the side supports to encase the ankle, and attachments adapted to engage said shoelaces to further encase the ankle, wherein the improvement comprises:

said pair of side supports each having a plurality of apertures therein for receiving said attachments;

said attachments each having an extended protuberance for engagement within a selected one of said plurality of apertures in said side support; and fasteners for securing said attachments within a selected one of said plurality of apertures in each side support.

2. The ankle brace of claim 1, wherein:
said plurality of apertures include a series of circular apertures aligned along an axis.

3. The ankle brace of claim 2, wherein:
said attachments each include a middle portion having a circular cross-section, a lower post portion extending from said middle portion to form said protuberance and a shoulder therebetween, and an upper head portion.

4. The ankle brace of claim 1, wherein:
said plurality of apertures includes slots having a plurality of notches therein.

5. The ankle brace of claim 4, wherein:
said notched slots include a plurality of semicircular serrations along one edge of each slot; and
said protuberances of said attachments are semicircular in cross-section for mating engagement with said notches in said slots.

6. The ankle brace of claim 5, additionally comprising:
said attachments each include a rectangular cross-sectional portion having side surfaces for engagement within said slots and a lower surface;
said semicircular protuberances each extend from a side surface of said rectangular cross-sectional portion for engagement within said notches in said slots;
said fasteners each include a post extending from each lower surface of said rectangular cross-sectional portion beyond said slot; and
said posts are adapted to be deformed to secure said attachments within said slots.

7. The ankle brace of claim 5, additionally comprising:
said attachments each include a rectangular cross-sectional portion having side surfaces for engagement within said slots and a lower surface;
said semicircular protuberances each extend from a side surface of said rectangular cross-sectional portion for engagement within said notches in said slots;
said lower surface of said rectangular cross-sectional portion including a threaded aperture therein; and
said fasteners included threaded posts for insertion into said threaded apertures for securing said attachments into said slots.

8. The ankle brace of claim 4, wherein:
said notched slots include a plurality of semicircular serrations along both edges of each slot; and
said protuberances of said attachments are circular in cross-section for mating engagement with said notches in said slots.

9. The ankle brace of claim 8, wherein:
said attachments each include a middle portion having a circular cross-section, a lower post portion extending from said middle portion to form said protuberance and a shoulder therebetween, and an upper head portion.

10. The ankle brace of claim 1, wherein:
said fasteners are extended portions of said attachments which may be deformed to rivet said attachments into said selected one of said plurality of apertures.

11. The ankle brace of claim 1, wherein:
said fasteners are threaded fasteners for securing said attachments into said selected one of said plurality of apertures.

12. The ankle brace of claim 1, additionally comprising:
said attachments each having an upper portion formed to include an eyelet for engaging said shoelaces.

13. The ankle brace of claim 12, wherein:
said eyelet is formed from a D-shaped ring.

14. The ankle brace of claim 12, wherein:
said eyelet is formed as a unitary molded piece with said attachments.

15. The ankle brace of claim 1, additionally comprising:
said attachments each having an upper portion formed as a shoe hook for engaging said shoelaces.

16. The ankle brace of claim 1, additionally comprising:
a plurality of said attachments mounted within each notched slot.

17. In an ankle brace for insertion into a laced shoe for restricting inversion and eversion of the ankle, said brace having side supports for supporting the ankle, and attachment straps to secure the side supports, wherein the improvement comprises:

said side supports each having a slot therein with at least one edge thereof serrated by a plurality of notches;

attachments mounted within said slots, said attachments each having an upper and middle portion, said middle portion having a protuberance extending therefrom for engagement with said notch in said slot; and fasteners attached to said middle portion of said attachments for securing said attachments in a selected one of said semicircular notches.

18. The ankle brace of claim 17, wherein:
said fasteners are formed from a lower portion of said attachments which are deformable to rivet said attachments into said slots at said selected semicircular notch.

19. The ankle brace of claim 17, additionally comprising:
said middle portions of said attachments having lower surfaces which include threaded apertures therein; and
said fasteners are threaded for mating engagement with said threaded apertures to selectively secure said attachments into said slots at said semicircular notches.

20. The ankle brace of claim 17, wherein:
said attachments include eyelets to engage said laces.

21. The ankle brace of claim 17, wherein:
said attachments include shoe hooks to engage said laces.

22. The ankle brace of claim 17, wherein:
said attachments include an extended head portion to engage said laces.

23. In an ankle brace for insertion into a laced show for restricting inversion and eversion of the ankle, said brace having side supports for supporting the ankle; attachment straps to secure the side supports, wherein the improvement comprises:

said side supports each having a plurality of apertures therein;

attachments mounted within selected apertures on each side support;

said attachments having a lower post portion extending through said selected apertures adapted to be deformed to secure said attachments within said selected apertures; and said attachments having an extended head portion for engaging said laces.

* * * * *